United States Patent
Watanabe et al.

(10) Patent No.: US 7,381,955 B2
(45) Date of Patent: Jun. 3, 2008

(54) METHOD AND APPARATUS FOR INSPECTING TARGET BY TERA-HERTZ WAVE SPECTROMETRY

(75) Inventors: Yuki Watanabe, Wako (JP); Kodo Kawase, Wako (JP); Tomofumi Ikari, Wako (JP)

(73) Assignee: Riken, Saitama (JP)

( * ) Notice: Subject to any disclaimer, the term of this patent is extended or adjusted under 35 U.S.C. 154(b) by 141 days.

(21) Appl. No.: 10/550,303

(22) PCT Filed: Mar. 18, 2004

(86) PCT No.: PCT/JP2004/003634

§ 371 (c)(1),
(2), (4) Date: Sep. 22, 2005

(87) PCT Pub. No.: WO2004/086011

PCT Pub. Date: Oct. 7, 2004

(65) Prior Publication Data

US 2006/0219922 A1     Oct. 5, 2006

(30) Foreign Application Priority Data

Mar. 25, 2003   (JP)   ............... 2003-082466

(51) Int. Cl.
*G01J 3/42* (2006.01)
(52) U.S. Cl. .................................. 250/341.8
(58) Field of Classification Search ............. 250/341.8, 250/252.1
See application file for complete search history.

(56) References Cited

U.S. PATENT DOCUMENTS

| | | | | |
|---|---|---|---|---|
| 5,623,145 A | * | 4/1997 | Nuss ........................ | 250/330 |
| 5,939,721 A | * | 8/1999 | Jacobsen et al. ............ | 250/330 |
| 6,015,667 A | * | 1/2000 | Sharaf ........................ | 435/6 |
| 6,078,047 A | * | 6/2000 | Mittleman et al. ........ | 250/338.1 |
| 6,957,099 B1 | * | 10/2005 | Arnone et al. .............. | 600/473 |
| 7,119,339 B2 | * | 10/2006 | Ferguson et al. ......... | 250/358.1 |
| 7,129,491 B2 | * | 10/2006 | Ferguson et al. ......... | 250/341.1 |

(Continued)

FOREIGN PATENT DOCUMENTS

JP        01-242941        9/1989

(Continued)

OTHER PUBLICATIONS

Jiang Z., Zhang X.; Terahertz Imaging Via Electrooptic Effect; Dec. 1999; IEEE Transactions On Microwave Theory And Techniques; vol. 47; No. 12; pp. 2644-2650.*

(Continued)

*Primary Examiner*—David P. Porta
*Assistant Examiner*—David S Baker
(74) *Attorney, Agent, or Firm*—Griffin & Szipl, P.C.

(57) ABSTRACT

A method includes a spectroscopic measurement step of pre-measuring a spectrum [S] of tera-hertz wave absorbencies of a target component for a plurality of frequencies ranging about from 1 THz to 3 THz, and an object spectroscopic step of irradiating an object with tera-hertz waves of the plurality of frequencies to measure absorbencies I of the object. Presence and absence of the target component in the object is determined on the basis of the spectrum [S] of the absorbancy S and the spectrum [I] of the absorbancy I of the object.

23 Claims, 5 Drawing Sheets

U.S. PATENT DOCUMENTS

| | | | |
|---|---|---|---|
| 2003/0149346 A1* | 8/2003 | Arnone et al. | 600/309 |
| 2004/0061055 A1* | 4/2004 | Kawase et al. | 250/330 |
| 2005/0116170 A1* | 6/2005 | Kawase et al. | 250/341.1 |
| 2006/0022140 A1* | 2/2006 | Connelly et al. | 250/338.1 |
| 2006/0056586 A1* | 3/2006 | Uetake et al. | 378/57 |
| 2006/0244629 A1* | 11/2006 | Miyazaki et al. | 340/855.7 |
| 2006/0255277 A1* | 11/2006 | Cole et al. | 250/341.1 |
| 2006/0268945 A1* | 11/2006 | Minamide et al. | 372/6 |
| 2007/0108382 A1* | 5/2007 | Itsuji | 250/330 |
| 2007/0228280 A1* | 10/2007 | Mueller | 250/341.1 |
| 2007/0263682 A1* | 11/2007 | Zhang et al. | 372/25 |

FOREIGN PATENT DOCUMENTS

| | | |
|---|---|---|
| JP | 2002-072269 | 3/2002 |
| JP | 2003-005238 | 1/2003 |
| WO | WO 97/46963 | 12/1997 |

OTHER PUBLICATIONS

International Search Report completed Apr. 7, 2004 and mailed Apr. 20, 2004 in corresponding International Application No. PCT/JP2004/003634.

Kawata, S. et al., "Component Analysis of Spatial and Spectral Patterns in Multispectral Images. I. Basis", J. Opt. Soc. Am. A., vol. 4, No. 11, pp. 2101-2106, Nov. 1987.

Sasaki, K. et al., "Component Analysis of Spatial and Spectral Patterns in Multispectral Images. II. Entropy minimization", J. Opt. Soc. Am. A., vol. 6, No. 1, pp. 73-79, Jan. 1989.

Kawata, S. et al., "Image Process for Scientific Instrument", Chapter 11, Color Image and Image Spectroscopy, Publisher CQ, pp. 259-265.

Yoshiharu, Izumi, "Guidance for Equipment Analysis", Chapter 1, "Infrared Absorption Spectrum Method", Kagaku Dojin pp. 1-20.

Supplementary European Search Report issued in corresponding application No. EP 04 72 1679, completed Dec. 18, 2006 and mailed Jan. 12, 2007.

Hadjiloucas, Sillas et al., "Analysis of spectroscopic measurements of leaf water content at terahertz frequencies using linear transforms," J. Opt. Soc. Am. A., vol. 19, No. 12, Dec. 2002, pp. 2495-2509.

Shen, Y.G. et al., "Determination of Glucose Concentration in Whole Blood using Fourier-Transform Infrared Spectroscopy," Journal of Biological Physics 29, 2003, pp. 129-133.

Wang, Shaohong et al., "Powder Detection Using THz Imaging," Monday Afternoon/Cleo 2002, p. 131, 2002.

Loeffler, Torsten et al., "Visualization and classification in biomedical terahertz pulsed imaging," Physics in Medicine and Biology 47, 2002, pp. 3847-3852.

Koch, Martin, "THz-Imaging: Fundamentals and Biological Applications," EUROPTO Conference on Terhertz Spectroscopy and Applications II, SPIE vol. 3828, 1999, pp. 202-208.

Hu, B.B. et al., "Imaging with terahertz waves," Optics Letters, vol. 20, No. 16, Aug. 15, 1995, pp. 1716-1719.

Weiss, C. et al., "Einsatz breitbandiger THz-Strahlung in der Gasanalyse—Broadband THz-Radiation for Gas Analysis," Technisches Messen 68, 2001, pp. 388-399.

Watanabe, Y. et al., "Component spatial pattern analysis of chemicals using terahertz spectroscopic imaging," Applied Physics Letters, vol. 83, No. 4, Jul. 28, 2003, pp. 800-802.

Kawase, Kodo et al., "Non-destructive terahertz imaging of illicit drugs using spectral fingerprints," Optics Express, vol. 11, No. 20, Oct. 6, 2003, pp. 2549-2554.

Taday, Philip F., "Applications of terahertz spectroscopy to pharmaceutical sciences," Phil. Trans R. Soc. Lond, A, No. 362, 2004, pp. 351-364.

Matthias, Otto, "Chemometrics: Statistics and Computer Application in Analytical Chemistry (6.2 Multiple linear regression)," 1999, pp. 192-207.

* cited by examiner

FIG.6A
1.2 THz

FIG.6B
1.3 THz

FIG.6C
1.4 THz

FIG.6D
1.5 THz

FIG.6E
1.6 THz

FIG.6F
1.7 THz

FIG.6G
1.8 THz

FIG.6H
1.9 THz

FIG.6I
2.0 THz

0    $-\ln(It/I0)$    4.9

FIG.7A
5-ASPIRIN

FIG.7B
PALATINOSE

METHOD AND APPARATUS FOR INSPECTING TARGET BY TERA-HERTZ WAVE SPECTROMETRY

This is a National Phase Application in the United State of International Patent Application No. PCT/JP2004/003634 filed Mar. 18, 2004, which claims priority on Japanese Patent Application No. 082466/2003, filed Mar. 25, 2003 The entire disclosures of the above patent applications are hereby incorporated by reference.

BACKGROUND OF THE INVENTION

1. Field of the Invention

The present invention relates to a method and apparatus for inspecting a target by tera-hertz wave spectrometry.

2. Description of the Related Art

A frequency of a far infrared ray or submillimeter wave which ranges about from 0.5 to 3 THz is positioned at the boundary between the frequency range of a light wave and the frequency range of a radio wave. The technology for a light wave and the technology for a radio wave have been advanced respectively. On the other hand, the technology for a far infrared ray or submillimeter wave has not been cultivated from the standpoint of technical advancement and its technical application. However, recently, it is becoming more important to effectively use the frequency range of about 0.5 to 3 THz in radio communication, apply this frequency range to ultrahigh-speed communication, and take advantage of characteristics of an electromagnetic wave of this frequency region for inspecting environment by imaging or tomography. In the following, this frequency region (about 0.5 to 3 THz) of a far infrared ray or submillimeter wave is referred to as a tera-hertz wave.

Patent Literatures 1 and 2, for example discloses means for generating a tera-hertz wave. Non-Patent Literatures 1, 2 and 3 are other documents related to a tera-hertz wave.

[Non-Patent Literature 1]

S. Kawata, K. Sasaki, and S. Minami, "Component analysis of spatial and spectral patterns in multispectral images. I.Basis," J.Opt.Soc.Am.A4, 2101(1987).

[Non-Patent Literature 2]

K. Sasaki, S. Kawata, and S. Minami, "Component analysis of spatial and spectral patterns in multispectral images. II.Entropy minimization," J.Opt.Soc.Am.A6, 73(1989).

[Non-Patent Literature 3]

S. Kawata, and S. Minami, "Image Process for Scientific Instrument", Chapter 11, Color Image and Image Spectroscopy, Publisher CQ, P 259-265.

[Non-Patent Literature 4]

Izumi Yoshiharu, "Guidance for Equipment Analysis", Chapter 1, Infrared Absorption Spectrum Method", Kagaku Dojin P 1-20.

[Patent Literature 1]

Japanese Laid-Open Patent Publication No. 2002-72269

[Patent Literature 2]

Japanese Laid-Open Patent Publication No. 2003-5238

One of characteristics of a tera-hertz wave is that the wavelength is not only within the range of the shortest wavelength of a radio wave that propagates through a material, but also within the region of the longest wavelength of a light wave that propagates straight. In other words, a tera-hertz wave can penetrates through various materials like a radio wave, and provide the highest space resolution in a radio wave, and be guided by a lens or mirror like a light wave.

Thus, a tera-hertz wave can penetrates through a semiconductor, plastic, paper, rubber, vinyl, wood, textile, ceramics, concrete, a tooth, a bone, fat, dried food, ice, and so on. For this reason, a tera-hertz wave is expected as imaging means that is an alternative to a X-ray and is safe for a human body.

Recently, one of a terrorist act that anthrax bacteria or drug is distributed by mail was raised as a social problem. The shape of an object enclosed in an envelope can be determined by conventional X ray, but the property of the object in the envelope cannot be determined unless the envelope is opened. Accordingly, when powdery anthrax bacteria or drug is enclosed in an envelope, any abnormality cannot be detected by X ray photograph.

SUMMARY OF THE INVENTION

The present invention was made to solve the above problems. That is, it is an object of the present invention to provide a target inspecting method and apparatus that can determine the contents component inside a mail article or the like and the shape of the contents that were not determined by a conventional X ray photograph, without opening the mail article.

According to the present invention, there is provided a method of inspecting a target by tera-hertz wave spectroscopic measurement, comprising:

a spectroscopic measurement step of pre-measuring a spectrum [S] of tera-hertz Wave absorbencies of a target component for a plurality of frequencies ranging about from 1 THz to 3 THz; and an object spectroscopic step of irradiating an object with tera-hertz waves of the plurality of frequencies to measure absorbencies I of the object, wherein presence and absence of the target component in the object is determined on the basis of the spectrum [S] of the absorbancy S and the spectrum [I] of the absorbancy I of the object.

According to a preferred embodiment of the present invention, the method comprises a density calculation step of calculating a target density [P] on the basis of the spectrum [S] of the absorbancy S and the spectrum [I] of the absorbancy I of the object.

Further, the target spectroscopic step comprises a step of two-dimensionally scanning the object with the tera-hertz waves to measure a two-dimensional distribution [I] of the absorbancy I of penetration light, and the density calculation step comprises a step of calculating a two-dimensional distribution [P] of the target density P.

Furthermore, according to the present invention, there is provided an apparatus for inspecting a target using tera-hertz wave spectroscopic measurement, comprising:

a tera-hertz wave generation device (12) that generates tera-hertz waves (4) of a plurality of wavelengths;

a two-dimensional scan device (18) that scans an object (10) with the tera-hertz waves of the plurality of wavelengths, a spectroscopic measurement device (14) that measures a two-dimensional distribution [I] of light absorbancy I of the object; and a target density calculation device (16) that calculates a two-dimensional distribution [P] of a target density P on the basis of a pre-measured spectrum [S] of light absorbancy S of a target and the two-dimensional distribution [I] of the light absorbancy I.

By the above method and apparatus, tera-hertz waves (4) of a plurality of different wavelengths are generated by the tera-hertz wave generation device (12), the object (10) is scanned with the terahertz waves (4) by the two-dimensional scan device (18), and the two-dimensional distribution [I] of the absorbancy I of the object is measured by the spectroscopic measurement device (14) so that the two-dimensional distribution [P] of the target density P can be calculated on the basis of the pre-measured spectrum [S] of the absorbancy S of the target and the two-dimensional distribution [I] of the absorbency I by imaging spectroscopy, using the target density calculation apparatus.

Accordingly, it is possible to determine the component of the contents inside a mail article or the like without opening the mail article when the component has a tera-hertz wave absorbancy depending on the wavelength. Furthermore, it is possible to determine abnormality of the inside contents that was not determined by a conventional x ray photograph.

In addition, the apparatus comprises an image display device (20) that two-dimensionally displays an image of the two-dimensional distribution [P] of the target density P. The image of the two-dimensional distribution [P] of the target density P is two-dimensionally displayed so that the shape of the target having a wavelength-dependent property in the object (10) can be two-dimensionally displayed together with the distribution of the target.

The tera-hertz waves of N number of different wavelengths are used for M number of targets, N being equal to or larger than M, when N is equal to M, the two-dimensional distribution [P] of the target density P is calculated by $[P]=[S]^{-1}[I]$, and when N is larger than M, the two-dimensional distribution [P] of the target density P is calculated by $[I]=[S][P]$, using a least square method.

Thereby, even when a plurality of targets exist, the shapes of the targets having the wavelength-dependent property in the object (10) as well as the distributions of the targets can be two-dimensionally displayed in a short time by processing the image of the two-dimensional distribution [I] of the light absorbancy, using a general-purpose personal computer.

Other objects and advantageous features of the present invention will become apparent from the following description with reference to the accompanying drawings.

DESCRIPTION OF THE PREFERRED EMBODIMENTS

In the following, a preferred embodiment of the present invention will be described with reference to the drawings.

In the drawings, the same reference numeral is attached to the common parts, and the overlapping description will be omitted.

Figure 1:
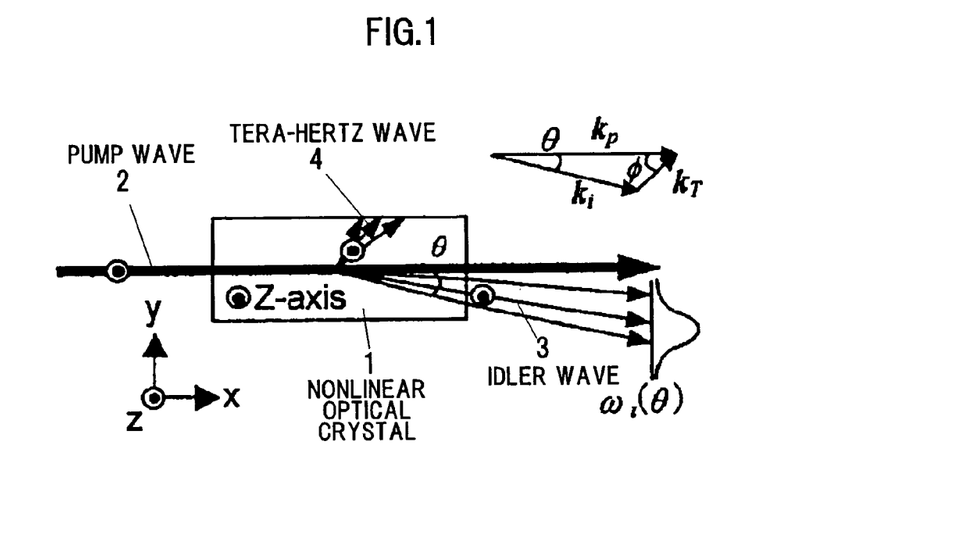
FIG. 1 shows a principle of generation of a tera-hertz wave.

FIG. 1 shows a principle of tera-hertz wave generation. In FIG. 1, the reference numeral 1 designates a nonlinear optical crystal (for example, $LiNbO_3$), the reference numeral 2 a pump wave (for example, YAG laser beam), the reference numeral 3 a idler wave, and the reference numeral 4 a tera-hertz wave.

When the pump wave 2 enters, in a certain direction, the nonlinear optical crystal 1 having Raman activity and far infrared activity, the idler wave 3 and the tera-hertz wave 4 are generated via an elementary excitation wave (polariton) of the material by induced Raman effect (or the parametric interaction). In this case, an energy conservation law expressed by the equation (1) and a momentum conversation law expressed by the equation (2) are established among the pump wave 2 ($\omega_p$), the tera-hertz wave 4 ($\omega_T$), and the idler wave 3 ($\omega_i$). In the equation (2), each term is a vector, and the non-collinear phase matching condition can be expressed as indicated by the illustration at the upper right in FIG. 1.

$$\omega_p = \omega_T + \omega_i \quad (1)$$

$$\kappa_p = \kappa_T + \kappa_i \quad (2)$$

The generated idler wave 3 and the tera-hertz wave 4 have spatial extent, and the wavelengths of the idler wave 3 and the tera-hertz wave 4 continuously vary in accordance with the output angle. The generation of this broad idler wave 3 and tera-hertz wave 4 in the single path arrangement is referred to as TPG (THz-wave Parametric Generation).

The basic parametric process is defined by extinction of one pump photon, and the simultaneous generation of one idler photon and one signal photon. When the idler light or the signal light resonates, and the intensity of the pump light exceeds a threshold value, parametric generation occurs. The induced Raman scattering is defined by the extinction of one pump photon, the simultaneous generation of one idler photon and one polariton. The induced Raman scattering is included in the broad-defined parametric interaction.

However, the tera-hertz wave generated by a tera-hertz wave generation device of the single path arrangement is very weak. Furthermore, a large part of the generated tera-hertz wave is absorbed when the tera-hertz wave advances in the nonlinear optical crystal by several-hundred microns.

Figure 2:
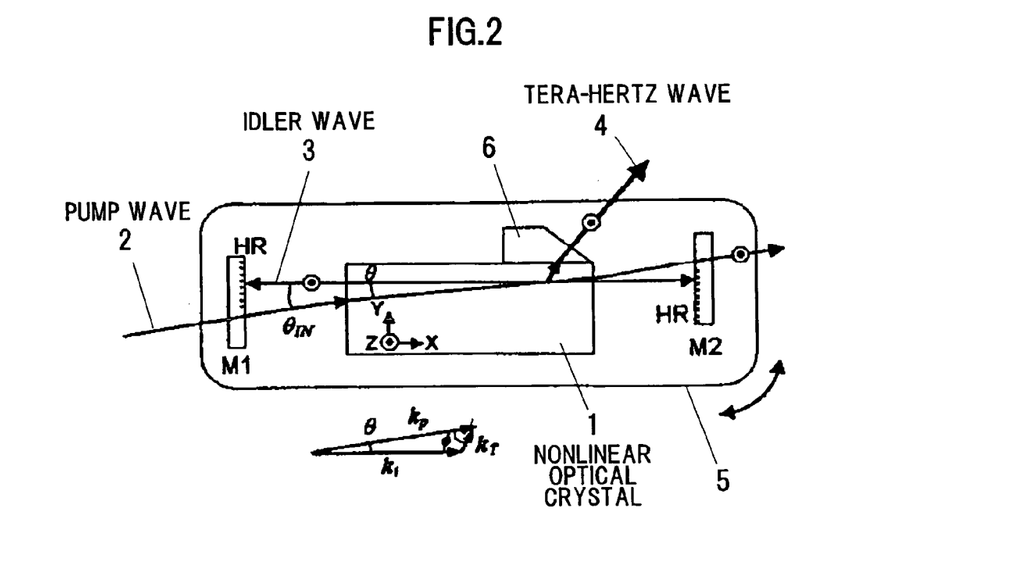
FIG. 2 shows the configuration of a tera-hertz wave generation device having a resonator.

FIG. 2 shows the configuration of a tera-hertz wave generation device that solves this problem. As shown in FIG. 2, the resonator is arranged in the specific direction (angle θ) relative to the broad idler wave 3 so as to increase the intensity of the idler wave 3 in the specific direction. In this case, the resonator includes mirrors M1 and M2 having high reflective coats, and is disposed on a rotary stage 5 such that the angles of the resonator can be adjusted. The high reflective coat is formed on one half part of each of the two mirrors M1 and M2 such that the pump wave 2 can penetrate through the other half of each of the mirrors M1 and M2. In FIG. 2, the reference numeral 6 designates a prism coupler for extracting the tera-hertz wave 4 to the outside.

In the tera-hertz wave generation device shown in FIG. 2, when an incident angle θ of the pump wave to the crystal is changed within a certain range (for example, 1 to 2 degrees), an angle of the pump wave made with the idler wave is changed, and an angle of the tera-hertz wave made with the idler wave is also changed. By this phase matching condition change, the wavelength of the tera-hertz wave can be continuously changed between about 140 microns to about 310 microns, for example.

Figure 3:
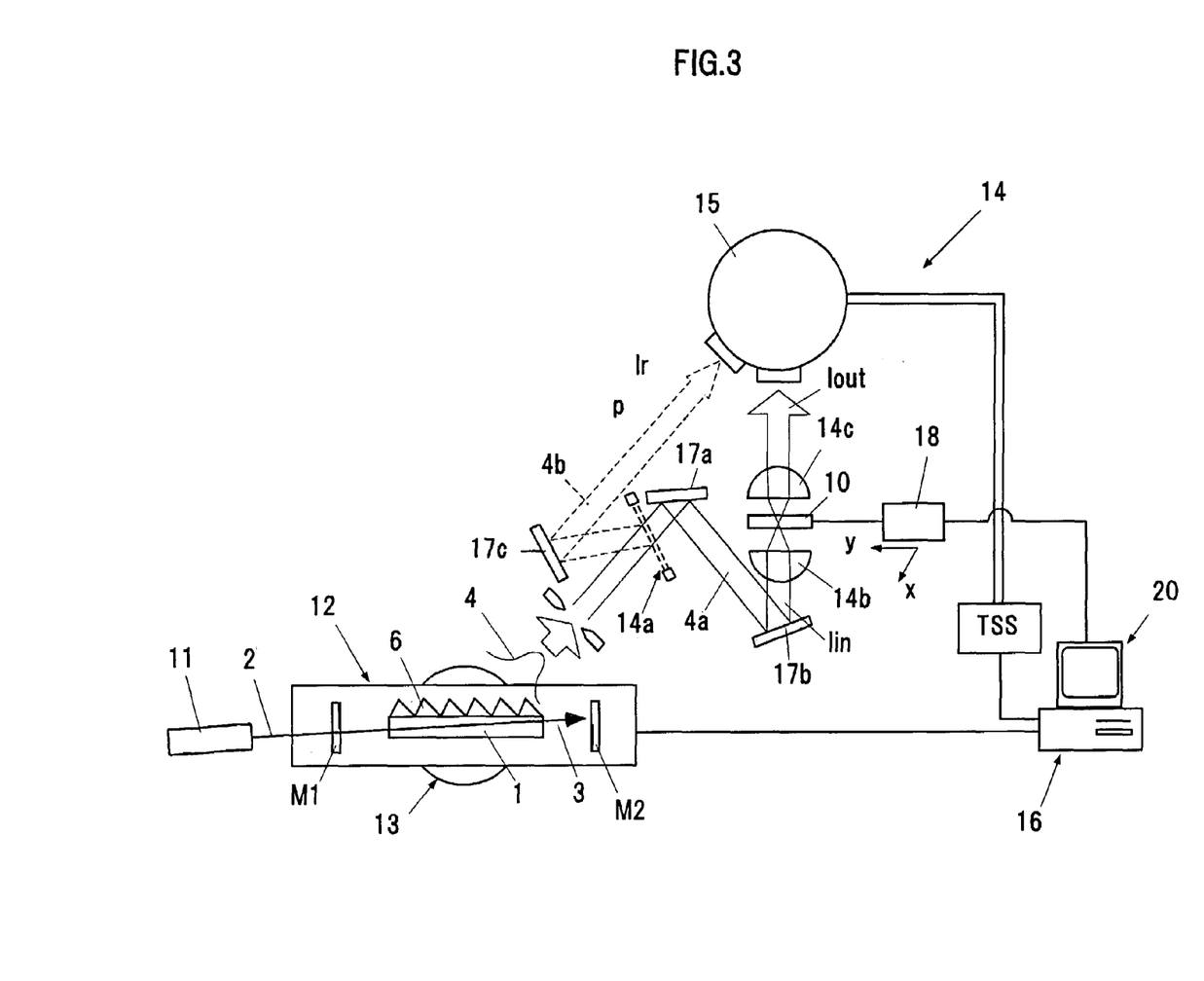
FIG. 3 shows the entire configuration of a target inspecting apparatus according to the present invention.

FIG. 3 shows the entire configuration of a target inspecting apparatus according to the preferred embodiment of the present invention. In FIG. 3, the target inspecting apparatus includes the tera-hertz wave generation device 12, a spectroscopic measurement device 14, a target density calculation device 16, a two-dimensional scan device 18, and an image display device 20.

The tera-hertz wave generation device 12 includes the nonlinear optical crystal 1 capable of generating the tera-hertz wave by the parametric effect, a pump wave introducing device that introduces the pump wave 2 to the nonlinear optical crystal 1 to generate the idler wave 3 and the tera-hertz wave 4, and a switching device 13 that changes the wavelength of the generated tera-hertz wave 4.

In this example, the tera-hertz wave generation device 12 is the tera-hertz wave generation device shown in FIG. 2. In this example, the switching device 13 a rotary stage that rotates a stage on which the mirrors M1 and M2 are disposed so as to change the incident angle θ of the pump light to the crystal.

According to the tera-hertz wave generation device 12, operating the switching device 13 (the rotary stage) enables the generation of the tera-hertz waves having different wavelengths in the tera-hertz region of about 1 THz to 3 THz.

In FIG. 3, the spectroscopic measurement device 14 includes a divider 14a, a condenser lens 14b, and a spectroscopic measurement unit 15.

The divider is a wire grid in this example, and divides the tera-hertz wave 4 into measurement light 4a and reference light 4b at a predetermined ratio. The measurement light 4a is introduced to the condenser lens 14b via reflective mirrors 17a and 17b. The reference light 4b is introduced to the spectroscopic measurement unit 15 via a reflective mirror 17c. The condenser lens 14b condenses the measurement light 4a on an object, and the measurement light 4a that has penetrated through the object reaches a scattering lens 14c where the diameter of the measurement light is enlarged. Then, the measurement light 4a is introduced to the spectroscopic measurement unit 15. The condenser lens 14b and the scattering lens 14c are TPX lenses having a focal length of about 30 mm. The spectroscopic measurement device 15 is a Si bolometer having two built-in detection elements, for example. The output of the spectroscopic measurement unit 15 is input to the target density calculation device 16.

The target density calculation device 16 is a personal computer having a storage unit, for example, and calculates the two-dimensional distribution of a target density on the basis of the pre-measured spectrum [S] of the light absorbancy S of a target and the two-dimensional distribution [I] of the light absorbancy I.

Even when the output fluctuation (ΔI) of the tera-hertz wave 4 exists, the output fluctuation (ΔI) is automatically compensated by using the reference light 4b. Thereby, the output fluctuation is corrected to always obtain accurate transmissivity of the object 10.

When the object 10 is a mail article, paper, plastic or textile that is the general internal contents of the mail article does not have tera-hertz wave absorption property that depends on the wavelength, that is, such general contents absorbs the tera-hertz wave at the same absorption rate for the different wavelengths.

On the other hand, a drug such as aspirin and vitamin, and bio-powder such as anthrax bacteria have the tera-hertz wave absorption property that depends on the wavelength, and absorbs the tera-hertz wave at the different absorption rates for the different wavelengths. Although the reason for this fact is not obvious, the reason is considered to be that the vibration frequency resulting from the molecular structure is close to the band of the tera-hertz wave.

Accordingly, on the basis of the difference in the transmissivity, the target density calculation device 16 can detect presence or absence of the target that has the tera-hertz wave absorption property depending on the wavelength. In the case of detecting the target that has the tera-hertz wave absorption property depending on the wavelength, this target can be opened in a safe apparatus to be examined.

The two-dimensional scan device 18 moves the object 10 in a x-y plane, for example, and two-dimensionally scans the surface of the object with the tera-hertz waves of a plurality of different wavelengths. The image display device 20 two-dimensionally displays the position detected by the target density calculating device 16 where the transmissivity is different between two wavelengths.

A method according to the preferred embodiment of the present invention uses the above-described target inspecting apparatus, and includes a spectrometric measurement step (A), an object spectrometric step (B), and a density calculation step (C).

At the spectrometric measurement step (A), the spectrum [S] of the absorbancy S is pre-measured for different wavelengths of about 1 THz to 3 THz, and the pre-measured spectrum [S] is stored.

At the spectrometric measurement step (B), the object is irradiated with the tera-hertz-waves of the respective wavelengths to measure the absorbancy I of the object. At this step (B), it is preferable to two-dimensionally scan the object with the tera-hertz wave to measure the two-dimensional distribution [I] of the absorbancy I for the penetration light.

At the density calculation step (C), the target density P is calculated on the basis of the spectrum [S] of the absorbancy S and the absorbancy I. In the case of measuring the two-dimensional distribution [I] of the absorbancy I for the penetration light, the two-dimensional distribution [P] of the target density P is calculated at this step (C). The calculated two-dimensional distribution [P] of the target density P is two-dimensionally displayed by the image display device 20.

Figure 4:
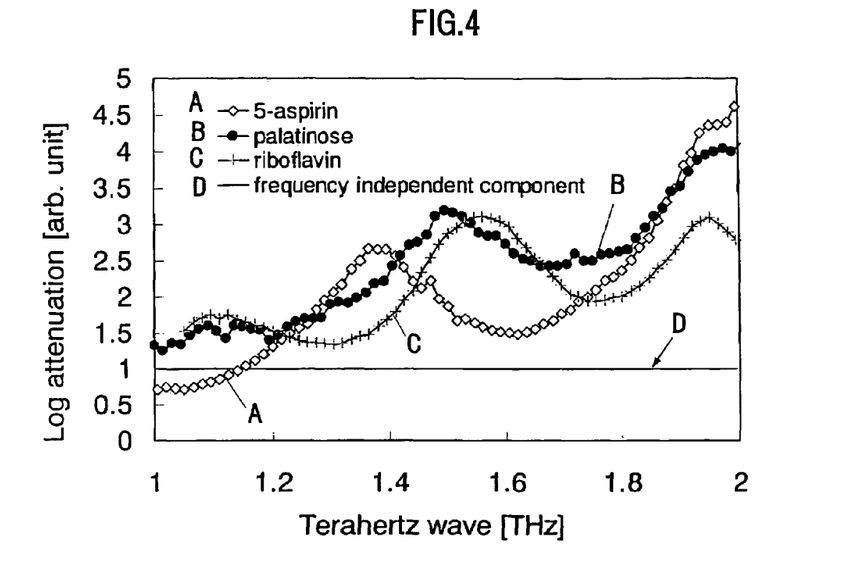
FIG. 4 shows the relation between the frequency of a tera-hertz wave and the light absorbancy of a target.

FIG. 4 shows the relation between the frequency of the tera-hertz wave and the absorbancy S of the target. In FIG. 4, the horizontal axis designates the frequency of the tera-hertz wave (THz), and the vertical axis designates the absorbancy log(I/IO) that is logarithm of the tera-hertz wave intensity I divided by the incident intensity.

As indicated by "D" in FIG. 4, when a sample is the general contents (paper, plastic or textile, for example) of a mail article, the attenuation (i.e., absorbency) is almost constant.

Meanwhile, in FIG. 4, the transmissivity (absorbency) change against the frequency (inverse number of wavelength) is different between 5-aspirin (A), palatinose (B) and riboflavin (C). Thus, FIG. 4 shows the tera-hertz wave absorption property depending on the wavelength. In the present invention, a material that exhibits such absorption property depending on the wavelength is a detection target.

A principle of the present invention will be described.

For the simplest example, it is assumed that the densities of two materials A and B having wavelength-dependent property are $P_A$ and $P_B$, respectively, the transmissivities of the material A for the wavelengths $\lambda_1$ and $\lambda_2$ are $S_A(\lambda_1)$ and $S_A(\lambda_2)$, respectively, and the transmissivities of the material B for the wavelengths $\lambda_1$ and $\lambda_2$ are $S_B(\lambda_1)$ and $S_B(\lambda_2)$, respectively. In this case, the absorbencies $I_1$ and $I_2$ of the penetration light of the wavelengths $\lambda_1$ and $\lambda_2$ are expressed by the equations (3) and (4).

$$I_1 = S_A(\lambda_1)P_A + S_B(\lambda_1)P_B \quad (3)$$

$$I_2 = S_A(\lambda_2)P_A + S_B(\lambda_2)P_B \quad (4)$$

In the equations (3) and (4), if $I_1$, $I_2$, $S_A(\lambda_1)$, $S_A(\lambda_2)$, $S_B(\lambda_1)$, and $S_B(\lambda_2)$ are known, the densities $P_A$ and $P_B$ of the two materials A and B can be obtained by solving the above simultaneous equations.

Similarly, it is assumed that the two-dimensional distributions of the densities of M number of materials are expressed by a matrix [P], the spectra of the absorbancies S against N number of different wavelengths for the respective materials are expressed by a matrix [S], and the two-dimensional distributions of the transmissivities of the penetration light against the respective wavelengths (frequencies) are expressed by a matrix [I]. On this assumption, the equation (5) can be established.

$$[I] = [S][P] \quad (5)$$

In this case, the image obtained by the tera-hertz waves of N frequencies can be expressed by a linear determinant as shown in the equation (6).

[Formula 1]

$$\begin{bmatrix} I(1,1) & \ldots & I(1,L) \\ \vdots & & \\ I(N,1) & \ldots & I(N,L) \end{bmatrix} = \begin{bmatrix} S(1,1) & & S(1,M) \\ \vdots & \ldots & \vdots \\ S(N,1) & & S(N,M) \end{bmatrix} \begin{bmatrix} P(1,1) & \ldots & P(1,L) \\ \vdots & & \vdots \\ P(M,1) & \ldots & P(M,L) \end{bmatrix} \quad (6)$$

In the equation (6), [I] is a matrix formed by horizontally arranging a one-dimensionally row vector $I(f_1)$, $I(f_2)$, ... $I(f_N)$, [P] is a matrix formed by vertically arranging the spectra of the respective materials, and [P] is a matrix formed by horizontally arranging vector expressions $P_1$, $P_2$, ... $P_N$ for the respective material patterns. In the equation (6), "L" designates the size of the image.

If [S] and [I] are known, [P] can be obtained from the equation (6).

In other words, in the case of N=M, the two-dimensional distributions [P] of the target densities P can be obtained by the equation $[P]=[S]^{-1}[I]$. Further, in the case of N>M, the two-dimensional distributions [P] can be calculated by the equation [I]=[S][P], using the least square method as shown in the equation (7).

[Formula 2]

$$[P] = ([S]^t[S])^{-1}[S]^t[I] \quad (7)$$

Embodied Example

In the following, an embodied example of the present invention will be described.

Figure 5:
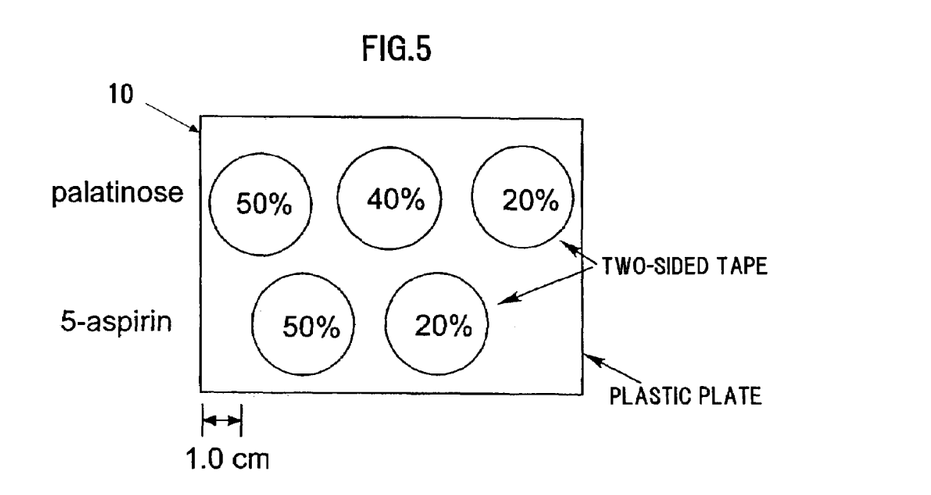
FIG. 5 schematically shows objects according to an embodiment of the present invention.
Figure 6A:
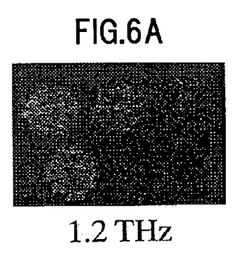
FIGS. 6A through 6I show penetration images captured for different frequencies of a tera-hertz wave.
Figure 6B:
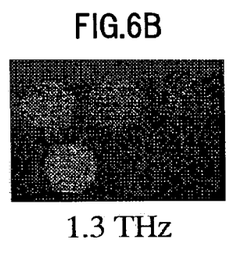
Figure 6C:
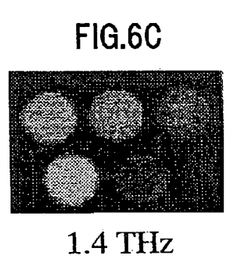
Figure 6D:
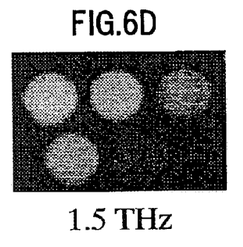
Figure 6E:
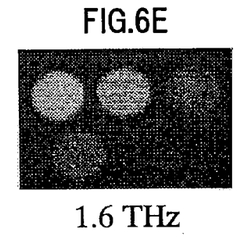
Figure 6F:
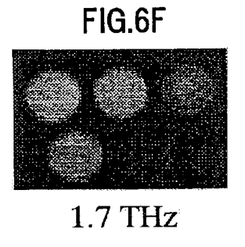
Figure 6G:
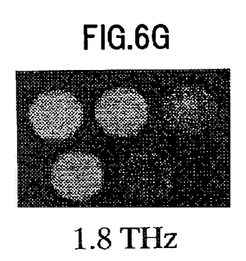
Figure 6H:
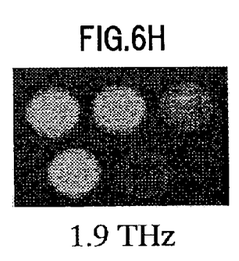
Figure 6I:
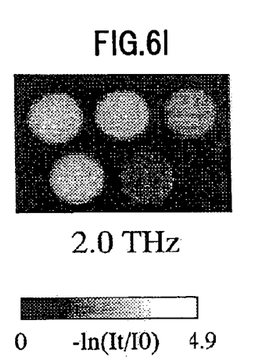

5 pieces of samples (pellets) were prepared as target materials by selecting palatinose and 5-aspirin shown in FIG. 4. The three of 5 pellets were mixtures of palatinose and polyethylene powder with the densities of palatinose being 50 percents, 40 percents and 20 percents, respectively. The other two of 5 pellets were mixtures of 5-aspirin and polyethylene powder with the densities of 5-aspirin being 50 percent and 20 percent, respectively. Each of 5 pellets had the same thickness of 1 mm and the same weight of 0.2 g. The 5 pellets as the objects 10 were attached on a thin plastic plate by a two-sided tape as shown in FIG. 5.

The relation spectra [S] between the wavelength (frequency) and absorbancy was measured for the pellets having the densities of 50 percents in the tera-hertz region of about 1.2 THz to 2.0 THz. The measured relation spectra were stored in the memory of the computer. These tera-hertz spectroscopic property were the same as shown in FIG. 4.

Next, by using the device shown in FIG. 3, the objects 10 were two-dimensionally scanned with the tera-hertz wave of 1.2 THz to 2.0 THz to measure the two-dimensional distributions of the absorbancies of the objects 10. The measured distributions were stored in the memory of the computer, and were displayed on the image display device 20.

FIGS. 6A through 6I show the penetration images of the objects 10 for the different frequencies. The scale for these images is the logarithm of the penetration tera-hertz wave intensity I divided by the incident tera-hertz wave intensity. It can be understood that dark and light coloring of these images of the 5 pellets is different between 1.2 THZ, 1.3 THz, 1.4 THz, 1.5 THz, 1.6 THz, 1.7 THz, 1.8 THz, 1.9 THz and 2.0 THz.

FIGS. 7A through 7D show density distributions of each material obtained from the 6 images of FIGS. 6B through 6G. When obtaining the density distributions, the matrix [S] of the spectroscopic data shown in FIG. 4 were used. Since the matrix [S] was measured by using samples having the densities of 50 percents, the obtained component patterns were multiplied by 50 percents to estimate the densities.

Figure 7A:
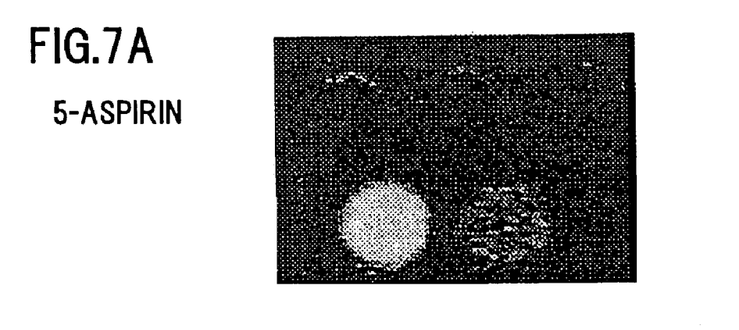
FIGS. 7A through 7D show density distributions of respective materials obtained from the 6 images of FIGS. 6A through 6I.
Figure 7B:
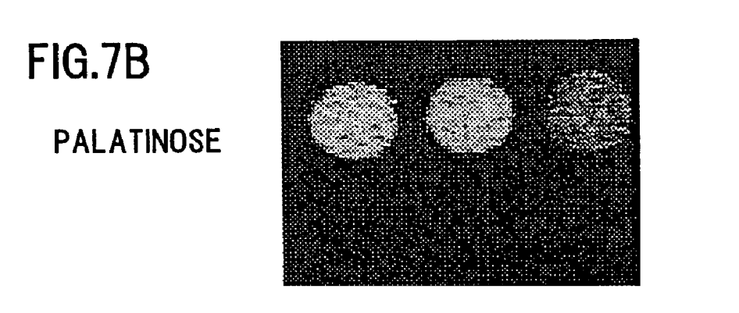
Figure 7C:
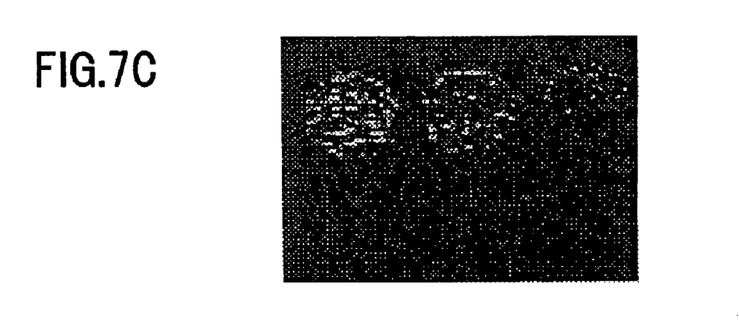
Figure 7D:
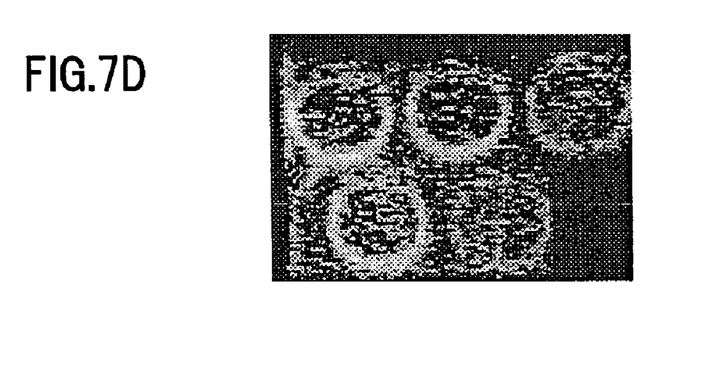

FIG. 7A shows the density distribution of 5-aspirine, FIG. 7B shows the density distribution of palatinose, FIG. 7C shows the density of riboflavin that was not contained in the objects 10, and FIG. 7D shows the density distribution of paper, plastic and so on that does not have wavelength dependence of absorbancy. From these figures, it is understood that the obtained density distributions depend on the components of the respective pellets constituting the objects 10. In other words, it is understood that the density difference as well as the components difference are extracted.

According to the method and apparatus of the present invention, the tera-hertz wave generation device 12 generates the tera-hertz waves 4 of the different wavelengths, the two-dimensional scan device 18 two-dimensionally scans the objects 10 with the tera-hertz waves, the spectroscopic measurement device 14 measures the two-dimensional distribution [I] of the absorbance of the objects, and the target density calculation device 16 calculates the two-dimensional distribution of the target density P by imaging spectroscopy on the basis of the pre-measured spectrum [S] of the target absorbance S and the two-dimensional distribution [I] of the absorbancy I.

Accordingly, when the object is a mail article that includes a target having wavelength-dependent property of tera-hertz wave absorbancy, it is possible to determine the component of the object included in the mail article without opening the mail article. Further, it is possible to detect abnormality of the object included in the mail article that was not detected by the conventional X ray photograph.

Furthermore, the device of the present invention includes the image display device 20 that two-dimensionally displays the two-dimensional distribution of the target density P. Thereby, the shape of the target having wavelength-dependent property of tera-hertz wave absorbancy included in the mail article can be displayed two-dimensionally together with the target density distribution.

According to the present invention, difference in component such as a chemical agent is extracted as a spatial pattern from a set of images measured by tera-hertz waves of different wavelengths, using known tera-hertz wave spectroscopic data. Thereby, it is possible to distinguish a component pattern of a material inside a parcel, an envelope, an opaque plastics container or the like.

Thus, the target inspecting method and apparatus using tera-hertz spectroscopic measurement has an excellent advantage in that an inside component and its shape that were not determined by the X ray photograph can be determined without opening the mail article.

The present invention is not limited to the above-described embodiment, and various modifications can be made without departing from the scope of the present invention.

What is claimed is:

1. A method of inspecting a target by tera-hertz wave spectroscopic measurement, comprising:
    a spectroscopic measurement step of pre-measuring a first spectrum matrix [S] of tera-hertz wave absorbencies of a target component for a plurality of frequencies ranging from about 1 THz to 3 THz;
    an object spectroscopic step of irradiating an object with tera-hertz waves of the plurality of frequencies to measure absorbencies of the object;
    determining presence or absence of the target component in the object on the basis of the first spectrum matrix [S] of tera-hertz wave absorbencies and a second spectrum matrix [I] of tera-hertz wave absorbencies of the object; and
    a density calculation step of calculating a target density [P] on the basis of the first spectrum matrix [S] of tera-hertz wave absorbencies and the second spectrum matrix [I] of tera-hertz wave absorbencies of the object.

2. A method of inspecting a target according to claim 1, wherein the target spectroscopic step comprises a step of two-dimensionally scanning the object with the tera-hertz waves to measure the two-dimensional distribution matrix [I] of absorbency of penetration light,
    and the density calculation step comprises a step of calculating the two-dimensional distribution matrix [P] of the target density, wherein tera-hertz waves of N number of different wavelengths are used for M number of targets, N being equal to or larger than M, wherein
    when N is equal to M, the two-dimensional distribution matrix [P] of the target density is calculated by [P]=[S]$^{-1}$[I],
    and when N is larger than M, the two-dimensional distribution matrix [P] of the target density is calculated by [I]=[S][P], using a least square method.

3. A method of inspecting a target according to claim 2, further comprising a step of two-dimensionally displaying the two-dimensional distribution matrix [P] of the target density.

4. A method of inspecting a target according to claim 2, further comprising a step of two-dimensionally displaying the two-dimensional distribution matrix [P] of the target density.

5. A method of inspecting a target according to claim 1, wherein the object is an article that is capable of containing the target component.

6. A method of inspecting a target according to claim 5, wherein the article is selected from the group consisting of an envelope, a parcel and a container.

7. A method of inspecting a target according to claim 5, wherein the target component is selected from the group consisting of a drug and bio-powder.

8. A method of inspecting a target according to claim 1, wherein tera-hertz waves of N number of different wavelengths are used for M number of targets, N being equal to or larger than M, wherein
    when N is equal to M, the two-dimensional distribution matrix [P] of the target density is calculated by [P]=[S]$^{-1}$[I],
    and when N is larger than M, the two-dimensional distribution matrix [P] of the target density is calculated by [I]=[S][P], using a least square method.

9. A method of inspecting a target according to claim 1, wherein determination of the presence or absence of the target component is performed without opening the object.

10. An apparatus for inspecting a target using tera-hertz wave spectroscopic measurement, comprising:
    a tera-hertz wave generation device that generates tera-hertz waves of a plurality of wavelengths;
    a two-dimensional scan device that scans an object with the tera-hertz waves of the plurality of wavelengths;
    a spectroscopic measurement device that measures a two-dimensional distribution matrix [I] of light absorbency of the object; and
    a target density calculation device that calculates a two-dimensional distribution matrix [P] of a target density on the basis of a pre-measured spectrum matrix [S] of light absorbency of a target and the two-dimensional distribution matrix [I] of light absorbency.

11. An apparatus for inspecting a target by tera-hertz wave spectroscopic measurement according to claim 10, wherein the target density calculation device determines a presence or absence of a target component in the object using the calculated two-dimensional distribution matrix [P] and without opening the object.

12. An apparatus for inspecting a target by tera-hertz wave spectroscopic measurement according to claim 11, wherein the object is an article that is capable of containing the target component.

13. An apparatus for inspecting a target by tera-hertz wave spectroscopic measurement according to claim 12, wherein the article is selected from the group consisting of an envelope, a parcel and a container.

14. An apparatus for inspecting a target by tera-hertz wave spectroscopic measurement according to claim 12, wherein the target component is selected from the group consisting of a drug and bio-powder.

15. An apparatus for inspecting a target by tera-hertz wave spectroscopic measurement, according to claim 10, further comprising an image display device that two-dimensionally displays an image of the two-dimensional distribution matrix [P] of the target density.

16. An apparatus for inspecting a target by tera-hertz wave spectroscopic measurement according to claim 10, wherein tera-hertz waves of N number of different wavelengths are used for M number of targets, N being equal to or larger than M, wherein the target density calculation device calculates the two-dimensional distribution matrix [P] as follows:
    when N is equal to M, the two-dimensional distribution matrix [P] of the target density is calculated by [P]=[S]$^{-1}$[I], and
    when N is larger than M, the two-dimensional distribution matrix [P] of the target density is calculated by [I]=[S][P], using a least square method.

17. A method of inspecting a target by tera-hertz wave spectroscopic measurement, comprising the steps of:

pre-measuring a first spectrum matrix [S] of tera-hertz wave absorbencies of a target component for a plurality of frequencies ranging from about 1 THz to 3 THz;

irradiating an object with tera-hertz waves of the plurality of frequencies to measure absorbencies of the object; and determining presence or absence of the target component in the object on the basis of the first spectrum matrix [S] of tera-hertz wave absorbencies and a second spectrum matrix [I] of tera-hertz wave absorbencies of the object.

18. A method of inspecting a target according to claim 17, wherein the object is an article that is capable of containing the target component.

19. A method of inspecting a target according to claim 18, wherein the article is selected from the group consisting of an envelope, a parcel and a container.

20. A method of inspecting a target according to claim 18, wherein the target component is selected from the group consisting of a drug and bio-powder.

21. A method of inspecting a target according to claim 17, further comprising the steps of:

calculating a target density on the basis of the first spectrum matrix [S] of tera-hertz wave absorbencies and the second spectrum matrix [I] of tera-hertz wave absorbencies of the object, wherein the target density is a two-dimensional distribution matrix [P], and pre-measuring the first spectrum matrix [S] comprises two-dimensionally scanning the object with the tera-hertz waves to measure a two-dimensional distribution matrix [I] of absorbency of penetration light; and two-dimensionally displaying the two-dimensional distribution matrix [P] of the target density.

22. A method of inspecting a target according to claim 17, wherein tera-hertz waves of N number of different wavelengths are used for M number of targets, N being equal to or larger than M, wherein when N is equal to M, the two-dimensional distribution matrix [P] of the target density is calculated by $[P]=[S]^{-1}[I]$, and when N is larger than M, the two-dimensional distribution matrix [P] of the target density is calculated by $[I]=[S][P]$, using a least square method.

23. A method of inspecting a target according to claim 17, wherein determination of the presence or absence of the target component is performed without opening the object.

* * * * *